US 6,639,402 B2

(12) United States Patent
Grimes et al.

(10) Patent No.: US 6,639,402 B2
(45) Date of Patent: Oct. 28, 2003

(54) TEMPERATURE, STRESS, AND CORROSIVE SENSING APPARATUS UTILIZING HARMONIC RESPONSE OF MAGNETICALLY SOFT SENSOR ELEMENT (S)

(75) Inventors: Craig A. Grimes, Boalsburg, PA (US); Keat Ghee Ong, State College, PA (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 10/061,840

(22) Filed: Jan. 31, 2002

(65) Prior Publication Data

US 2002/0153882 A1 Oct. 24, 2002

Related U.S. Application Data (60) Provisional application No. 60/265,373, filed on Jan. 31, 2001.

(51) Int. Cl.$^7$ .......................... G01N 27/00; G01K 7/00; G01L 1/12
(52) U.S. Cl. ....................... 324/239; 324/209; 324/232; 73/779; 436/149; 374/163
(58) Field of Search ................. 324/239, 209, 324/232, 262; 73/768, 779; 436/149; 374/117, 163

(56) References Cited

U.S. PATENT DOCUMENTS

| | | | |
|---|---|---|---|
| 4,510,489 A | 4/1985 | Anderson, III et al. | 340/572 |
| 4,561,314 A | 12/1985 | Alley et al. | 73/862.69 |
| 4,660,025 A | 4/1987 | Humphrey | 340/572 |
| 4,679,427 A | 7/1987 | Kanda et al. | 73/54 |
| 4,745,401 A | 5/1988 | Montean | 340/572 |
| 4,769,631 A | 9/1988 | Copeland | 340/551 |
| 4,817,430 A | 4/1989 | Benes et al. | 73/579 |
| 4,913,750 A | 4/1990 | Kakuno et al. | 148/304 |

(List continued on next page.)

FOREIGN PATENT DOCUMENTS

WO WO 97/04338 2/1997

OTHER PUBLICATIONS

Grimes, et al., 33–5 *IEEE Transactions on Magnetics* (Sep./1997) pp. 3412–3414.
Stoyanov, et al., 34–4 *IEEE Transactions on Magnetics* pp. 1315–1317 (Jul. 1998).
Barandiarán and Gutiérrez, 59 *Sensors and Actuators* A 38 (1997).
Barandiarán, et al., 5 *Int. J. of Applied Electromagnetics in Materials* 75 (1994).
Hansson, et al., 14 *Biosensors& Bioelectronics* (1999) pp. 671–682.

*Primary Examiner*—Walter E. Snow
(74) *Attorney, Agent, or Firm*—Macheldt Bales LLP (57) ABSTRACT

A temperature sensing apparatus including a sensor element made of a magnetically soft material operatively arranged within a first and second time-varying interrogation magnetic field, the first time-varying magnetic field being generated at a frequency higher than that for the second magnetic field. A receiver, remote from the sensor element, is engaged to measure intensity of electromagnetic emissions from the sensor element to identify a relative maximum amplitude value for each of a plurality of higher-order harmonic frequency amplitudes so measured. A unit then determines a value for temperature (or other parameter of interst) using the relative maximum harmonic amplitude values identified. In other aspects of the invention, the focus is on an apparatus and technique for determining a value for of stress condition of a solid analyte and for determining a value for corrosion, using the relative maximum harmonic amplitude values identified. A magnetically hard element supporting a biasing field adjacent the magnetically soft sensor element can be included.

28 Claims, 5 Drawing Sheets

U.S. PATENT DOCUMENTS

| | | | |
|---|---|---|---|
| 4,980,670 A | 12/1990 | Humphrey et al. | 340/551 |
| 5,083,112 A | 1/1992 | Piotrowski | 340/572 |
| 5,130,697 A | 7/1992 | McGinn | 340/551 |
| 5,348,761 A | 9/1994 | Mitter et al. | 427/101 |
| 5,499,015 A | 3/1996 | Winkler et al. | 340/551 |
| 5,514,337 A | 5/1996 | Groger et al. | 422/82.08 |
| 5,538,803 A | 7/1996 | Gambino et al. | 428/694 TM |
| 5,552,778 A | 9/1996 | Schrott et al. | 340/825.34 |
| 5,554,974 A | 9/1996 | Brady et al. | 340/572 |
| 5,563,583 A | 10/1996 | Brady et al. | 340/572 |
| 5,565,847 A | 10/1996 | Gambino et al. | 340/572 |
| 5,585,772 A | 12/1996 | Joshi et al. | 335/215 |
| 5,597,534 A | 1/1997 | Kaiser | 422/82.08 |
| 5,621,316 A | 4/1997 | Dames et al. | 324/207.13 |
| 5,698,089 A | 12/1997 | Lewis et al. | 205/787 |
| 5,705,399 A | 1/1998 | Larue | 436/501 |
| 5,754,110 A | 5/1998 | Appalucci et al. | 340/572 |
| 5,821,129 A | 10/1998 | Grimes et al. | 436/151 |
| 5,841,350 A | 11/1998 | Appalucci et al. | 340/572 |
| 5,859,587 A | 1/1999 | Alicot et al. | 340/572 |
| 5,981,297 A | 11/1999 | Baselt | 436/514 |
| 6,018,988 A | 2/2000 | Persson | 73/54.25 |
| 6,359,444 B1 | 3/2002 | Grimes | 324/633 |
| 6,393,921 B1 | 5/2002 | Grimes et al. | 73/728 |
| 6,397,661 B1 | 6/2002 | Grimes et al. | 73/24.06 |

[Temperature response of Metglas 2826MB, 2605SC and 2714a]

FIG. 4

[Stress response of Metglas 2605SC, 2826MB, and 2714a]

FIG. 5

[Change in 2<sup>nd</sup> harmonic amplitude as a function of unstressed-stressed cycles, with increasing mass loads being applied to the sensor during the stress cycle. Both 2605SC and 2826MB show an irreversible response after stressed with a weight of 173 g.]

A 3-element sensor array

FIG. 10

[The response of a 3-element sensor array, where the sensor elements are biased at −5 Oe, 0 and 5 Oe, respectively]

TEMPERATURE, STRESS, AND CORROSIVE SENSING APPARATUS UTILIZING HARMONIC RESPONSE OF MAGNETICALLY SOFT SENSOR ELEMENT (S)

This application claims priority to pending U.S. provisional patent application Ser. No. 60/265,373 filed by the assignee hereof on Jan. 31, 2001.

Reference to Assignee's Pending Applications for Magnetoelastic and RF Sensors

On Dec. 30, 1998, the assignee hereof filed a U.S. nonprovisional patent application for an applicant hereof, Dr. Craig Grimes, pending at the time of filing the instant application as Ser. No. 09/223,689 and issued on Jun. 4, 2002 as U.S. Pat. No. 6,387,661 entitled "Remote Magnetoelastic Analyte, Viscosity and Temperature Sensing Apparatus and Associated Methods of Sensing". On May 28, 1999, the assignee hereof filed a U.S. nonprovisional patent application for an applicant hereof, Dr. Craig Grimes, pending at the time of filing the instant application as Ser. No. 09/322,403 and issued on Mar. 19, 2002 as U.S. Pat. No. 6,359,444 entitled "Remote Resonant-Circuit Analyte Sensing Apparatus with Sensing Structure and Associated Method of Sensing." On Feb. 11, 2000, the assignee hereof filed a U.S. nonprovisional patent application for at least one applicant hereof, Dr. Craig Grimes, pending at the time of filing the instant application as Ser. No. 09/502,663 and issued on May 28, 2002, as U.S. Pat. No. 6,393,921 entitled "Magnetoelastic Sensing Apparatus and Method for Remote Pressure Query of an Environment." On Oct. 20, 2001, the assignee hereof filed a U.S. nonprovisional patent application for at least one applicant hereof, Dr. Craig Grimes, currently pending as Ser. No. 10/067,681 entitled "Magnetoelastic Sensor for Characterizing Properties of Thin-film/Coatings."

GOVERNMENT SUPPORT AND PRIORITY PROVISIONAL APPLICATION

The invention described herein was partially supported by the National Science Foundation under contract ECS-9988598, and by NASA under grant NAG-1-01036. Accordingly, the U.S. Government may have certain rights in this invention.

BACKGROUND OF THE INVENTION

Field of the Invention

In general, the present invention relates to temperature, stress, and chemical telemetry using sensing elements remotely located from associated electromagnetic (EM) emission pick-up and processing units that, in operation, detect emissions from the element. The invention targets temperature sensing, sensing and characterization of localized stress conditions of a solid analyte, and the monitoring one or more corrosive. More particularly, the invention is directed to a novel telemetering apparatus that employs a receiver to measure the intensity of electromagnetic emissions from a magnetically soft sensor element, whereby there is no hardwire connection between the receiver and the sensing element, and the receiver 'listens' for harmonics of the fundamental resonant frequency in order to carry out the temperature, stress, and corrosive monitoring telemetry. The invention is further directed to new telemetry techniques associated with the sensing apparatus of the invention, including: sensing temperature, determining stress conditions of a solid undergoing analysis, and sensing the presence or absence of, type, concentration of, or degradation caused over time by, one or more corrosive (such as chlorine) in a wide variety of environments. For example, the new apparatus provides a way to measure temperature, stress conditions, and corrosives, including: (a) sensing material degradation or localized permanent deformation (of single materials, composites, or laminates) caused by corrosion, temperature fluctuation, weather conditions, etc., thus, allowing for the identification of regions of actual or potential material fatigue and failure; (b) sensing internal or surface stress due to applied loads such as are experienced by construction materials (building or roadway), including repeated or prolonged exposure to a load, explosion, wind and weather conditions; (c) sensing temperature or corrosive concentration and/or type within a test sample or product packaging (during quality inspections/audit); and so on.

The new sensing element structures and technique provide information about a solid analyte or an environment utilizing the harmonic response of EM emissions of one or more sensor structures made of a magnetically soft sensing element. Furthermore, a magnetically hard (MH) element supporting a biasing field adjacent the magnetically soft sensing element can be included to provide additional functionalities, including: EM background noise; element ON-OFF switch; and biasing field response, where needed, by selective response of the MH element upon exposure to chemical species.

General Technical Background Discussion—Other Telemetry Devices

As is generally well known, electric and magnetic fields are fundamentally fields of force that originate from electric charges. Whether a force field may be termed electric, magnetic, or electromagnetic hinges on the motional state of the electric charges relative to the point at which field observations are made. Electric charges at rest relative to an observation point give rise to an electrostatic (time-independent) field there. The relative motion of the charges provides an additional force field called magnetic. That added field is magnetostatic if the charges are moving at constant to velocities relative to the observation point. Accelerated motions, on the other hand, produce both time-varying electric and magnetic fields termed electromagnetic fields. For general reference see the textbook, *Engineering Electromagnetic Fields and Waves*, Carl T. A. Johnk, John Wiley & Sons, $2^{nd}$ Edition (1988).

Anti-theft markers/tags (electronic article surveillance, EAS, markers) generally operate by "listening" for acoustic energy emitted in response to an interrogating AC magnetic field, to sense the presence of an EAS marker. Sensormatic, Inc. distributes an EAS tag (dimensions 3.8 cm×1.25 cm×0.04 mm) designed to operate at a fixed frequency of 58 kHz (well beyond the audible range of human hearing). These EAS tags are embedded/incorporated into articles for retail sale. Upon exiting a store, a customer walks through a pair of field coils emitting a 58 kHz magnetic field. If a tag is still in an article being carried by the customer, the tag will likewise emit a 58 kHz electromagnetic signal that can be detected using a pickup coil, which in turn may set off an audible or visual alarm. More-recently, these tags are being placed in a box-resonator, sized slightly larger than the tag, such as the tags placed within a cavity 20 of a housing (see FIG. 2 of Winkler et al.).

Winkler et al. describes an electronic article surveillance (EAS) anti-theft system that operates by detecting mechanical resonances of magnetostrictive elements made of amorphous metallic glass METGLAS® 2826 MB, to prevent or deter theft of merchandise from retail establishments. In response to an interrogation signal generated by energizing circuit 201, the interrogating coil 206 generates an interrogating magnetic field, which in turn excites the integrated marker portion 12 of the article of merchandise 10 into mechanical resonance. During the period that the circuit 202 is activated, and if an active marker is present in the interrogating magnetic field, such marker will generate in the receiver coil 207 a signal at the frequency of mechanical resonance of the marker. This signal is sensed by a receiver which responds to the sensed signal by generating a signal to an indicator to generate an alarm.

Anderson, III et al. discloses a marker 16 (FIG. 5) formed of a strip 18 of a magnetostrictive, ferromagnetic material adapted, when armed in its activated mode, to resonate mechanically at a frequency within the range of the incident magnetic field. A hard ferromagnetic element 44 disposed adjacent to the strip 18 is adapted, upon being magnetized, to magnetically bias the strip 18 and thereby arm it to resonate at that frequency. An oscillator provides an AC magnetic field within interrogation zone 12 to mechanically resonate a magnetostrictive strip 18, which has first been armed by a magnetized hard ferromagnetic element 44, upon exposure to this AC magnetic field. The sole object of Anderson, III et al. EAS marker is to detect the presence between coil units 22 and 24 (interrogation zone 12) of an "armed/activated" marker 16. In the event an activated marker 16 secured to a retail article is detected within zone 12, an alarm will sound. A deactivator system 38, electrically connected to a cash register, can be used to deactivate the marker.

Humphrey and, another reference, Humphrey et al. disclose a type of electronic article surveillance (EAS) marker which includes a thin strip or wire of magnetic material that, when exposed to an alternating interrogation signal of low frequency and low field strength, responds by generating a signal pulse that they state "causes a regenerative reversal of magnetic polarity generating a harmonically rich pulse that is readily detected and easily distinguished." And while the Humphrey references recognize that high harmonics are detectable for the low frequency interrogation fields they use, once again, it is simply the presence or absence of the EAS marker that is of any interest.

Schrott, et al. describes a multibit bimorph magnetic ID tag for attachment to, and identification of, an object. The tag has one or more bimorphs comprised of a thin strip of a magnetostrictive material attached to a thicker bar 21 of hard magnetic material. A shipping pallet, package, or product is tagged with the bimorph for later product identification. Schrott et al. indicates that a multibit tag could be programmed to generate a binary or other suitable code. In the binary code case, a certain frequency of an array of cantilevers can be assigned a value of "zero" or "one" and, if absent, it can take the opposite value. The Schrott, et al. ID tag is limited to coded (zeros and ones) identification of the object. If, in operation, a Schrott, et al. ID tag's resonant frequency (predetermined by size/materials) is not "hit" during interrogation due to some unexpected event/external factor (such as, its resonant frequency is changed due to a temperature swing, or due to reaction of the ID tag with a surrounding fluid), no response will be detected and an incorrect output code will result, thus, destroying the Schrott, et al. ID tag's function.

Rather than working at a fixed interrogation frequency and simply checking for amplitude like the anti-theft EAS markers do to sense presence or absence of an active EAS tag or marker on an article for purchase exposed to an interrogation field, the novel sensing apparatus and associated technique of the invention looks to the harmonic frequency response of a magnetically soft sensor element for information about temperature, stress conditions of a solid analyte, or a corrosive of interest. Operating as a telemeter, EM emissions are obtained through remote query according to the invention, without direct hard-wire connection and without the need to ensure the sensor element's orientation in order to provide such information. In effect, the high-frequency and low frequency time-varying interrogation fields to which the sensor element is exposed effectively empowers the 'passive' sensing element(s) of the invention, allowing for harmonic amplitude values of EM emissions to be identified.

SUMMARY OF THE INVENTION

It is a primary object of this invention to provide a telemetering apparatus for gathering information about temperature, stress conditions of a solid analyte, and corrosives within an environment or analyte, utilizing the harmonic frequency response of EM emissions from a magnetically soft sensing element upon concurrent exposure to high-frequency and low frequency interrogation fields. A receiver, remote from the magnetically soft element, is engaged to measure the intensity of EM emissions to identify a corresponding harmonic amplitude value, or series of values. A unit, such as a processor of suitable type, a computerized device having processing capability, and so on, is employed to determine a value for temperature, stress conditions, or corrosion (i.e., the value of interest) using the harmonic frequency amplitude value identified.

Advantages of providing the new sensing apparatus and associated technique, include without limitation:

(a) Mode of operation—The invention can be used for one-time disposable operation (e.g., in the form of a kit, whereby the sensor element is embedded within a solid analye or initially placed within packaging) or for continuous monitoring.

(b) Versatility of use—The apparatus may be used for individual measurements or on-going monitoring of temperature fluctuations, stress conditions, or a corrosive to allow for observation of characteristics of a solid analye (whether a single material or a composite or laminate) such as concrete, mortar, tar, wood, fiberboard, particleboard, plasterboard, sheetrock, fiberglass, plexiglass, resins, and plastics (including thermoplastics, and thermoformable, and thermoset plastics), as the analyte reacts to some agent, load, or other event over time, such as observing material degradation or deformation due to corrosion, exposure to a single catastrophic event (e.g., explosion or earthquake), repeated loads such as wind or auto travel (in the case of tarmac on roadways), weather conditions, and so on, thus, allowing for identification of material fatigue or failure in a nondestructive manner.

(c) Simplicity of use/Speed of results—The new sensing apparatus can produce measurement results, real-time, on-site with relative ease. The monitoring technique may be used alone or coupled with other current analysis methods such as visual inspection (in the case of buildings, fiberglass components of aircraft, roadways). Sensing data may be gathered within a few milli-seconds, or so.

(d) Apparatus design simplicity—Reducing the number and size of components required to accomplish measurements/monitoring reduces overall fabrication costs, making manufacturing economically feasible, and adds to ease of operation.

(e) Versatility of design—The sensor elements can be formed into many different shapes of various sizes; for example, the sensor elements may be fabricated on a small scale (a few millimeters) for use where space is extremely limited such as within small-sized sealed packaging or where embedded within a material, or on a larger scale (several centimeters). Several sensor elements may be incorporated or grouped into an array to provide a 'package' of various desired information or multiple parameters by sampling or measuring EM emission simultaneously or sequentially. This enables several measurements to be made with sensor element structures in an otherwise complex environment (e.g., a temperature measurement may be taken along with measurements relating to the concentration/presence/ absence of a corrosive).

Briefly described, once again, the invention includes a temperature sensing apparatus that includes a sensor element made of a magnetically soft material operatively arranged within a first and second time-varying interrogation magnetic field, the first time-varying magnetic field being generated at a frequency higher than that for the second magnetic field. Preferably, the second, lower frequency interrogation field is quasi-static, i.e., effectively operating as a dc (direct current) biasing field, selected to maximize the harmonic emission amplitudes measured from the sensor element in response to the higher frequency, first interrogation field.

A receiver, remote from the sensor element, is engaged to measure intensity of electromagnetic emissions from the sensor element to identify a relative maximum amplitude value for each of a plurality of higher-order harmonic frequency amplitudes so measured. A unit (comprising a processor, or other data processing device) is employed to determine a value for temperature using the relative maximum harmonic amplitude values identified. In another aspect of the invention, the focus is on an apparatus and technique for measurement EM emission intensity from a magnetically soft sensor element to determine a value for of stress condition of a solid analyte using the relative maximum harmonic amplitude values identified. In a third aspect of the invention, the focus is on an apparatus and technique for measurement of EM emission intensity from a magnetically soft sensor element to determine a value for corrosion using the relative maximum harmonic amplitude values identified.

There are many further distinguishing features of the apparatus and technique of the invention. The receiver can comprise an electromagnetic pick-up coil and associated EM emission detection circuitry such as a spectrum analyzer. The sensor element-maybe located within a solid analyte a component of which is a material selected from the group consisting of concrete, mortar, tar, wood, fiberboard, particleboard, plasterboard, sheetrock, fiberglass, plexiglass, resins, and plastics. The sensor element may be embedded within, located on a surface of, interposed between layers of, etc., the solid analyte so that, in operation, it can collect localized sensing information about the solid. The sensor element may be elongated in shape, having a length, e, from 1 mm to 1000 mm, and may be at least partially encapsulated within a corrosion-resistant casing if operated within an environment where reaction to an agent produces undesirable affects. A magnetically hard (MH) element supporting a biasing field adjacent the magnetically soft sensor element can be included. For example, the MH element may be made of a material chemically responsive to a fluid analyte such that exposure thereto causes a change in the biasing field.

The higher frequency of the first field may be selected from a first range of frequencies (50 Hz to 10 MHz) and the frequency of the second field may be selected from a second range of frequencies (0.1 Hz to 10 Hz). The second field of lower frequency is of an amplitude selected to correspond to offset that of a MH element's stray field, in the event a MH element is incorporated with the apparatus. The first, higher frequency interrogation field may be generated continuously over time (e.g., steady state over a selected time interval) or generated in the form of a pulse, or signal-burst of, for example, approximately 20 cycles generated at the higher frequency, during which time the measurement of EM emission intensity is made. Preferably the second, lower frequency interrogation field is generated continuously over the time period during which the high frequency field is generated so that EM emission intensity measurements can be taken to identify harmonic frequency amplitude values. It is the first, higher frequency field produced in conjunction with the quasi-static second time-varying field that provides a mechanism by which relative maximum amplitudes for the harmonic(s) of interest can be identified, thus, allowing for a value for the parameter of interest (temperature, stress conditions, corrosion) to be determined. By sweeping the second, quasi-static interrogation field amplitude, a relative maximum of the harmonic EM emissions of interest from the sensor element can be identified-this amounts to a 'tracking' of relative changes in EM emission intensity between several different higher-order harmonics to provide the parameter value (temperature, stress, corrosion) of interest.

The first and second interrogation fields may be transmitted by a single interrogation field generating coil or separate coils; one may choose to use a single coil to not only generate the first and second interrogation fields but also aid in the detection of EM emissions from the sensor element by operating as part (pick-up coil) of the receiver. Preferably the emissions measured and relative maximum harmonic frequency amplitude values identified are for higher-order harmonics ranging from, preferably, the $2^{nd}$ to $100^{th}$ harmonic of the fundamental resonant frequency for the sensor element.

A pre-correlation made between a series of comparative relative maximum harmonic amplitude values and a corresponding series of temperature, stress conditions, or corrosion values can be used to aid in calculation of the particular parameter value of interest. This pre-correlation can be earlier obtained using a calibration sensor element of like size and material characteristics of the sensor element used on-site, whereby the relative maximum higher-order harmonic frequency amplitudes identified, represented by a plurality of voltages corresponding to EM harmonic emission measurements, are collected and plotted against parameter values (e.g., temperature, stress, or corrosion) of interest. To automate on-going monitoring of a parameter, a computerized device To may be employed for instructing the receiver to take, over a time interval, a series of sensor element emission measurements, and communicate (or store for later use) each of a series of corresponding parameter values for these emission measurements taken. Further, a series of sensor element emission measurements may be taken over a selected response-time interval to produce a parameter response profile comprising a series of corresponding parameter values for the particular solid analyte.

The magnetically soft element is preferably made of a ferromagnetic alloy, including elements such as iron, cobalt, samarium, yttrium, gadolinium, terbium, or dysprosium. The element may take on a wide variety of shapes, including elongated ribbon shapes, rectangular-elongated, oval, elongated polygonal, etc., so long as the sensor element remains effectively magnetically soft thereby supporting a high magnetic permeability, allowing sufficient EM emission and remote receipt thereof according to the invention. For example, a width, w, that is less than three times a length, e, of the sensor element may be chosen.

BRIEF DESCRIPTION OF THE DRAWINGS

For purposes of illustrating the innovative nature plus the flexibility of design and versatility of the preferred apparatus and technique disclosed hereby, the invention will be better appreciated by reviewing the accompanying drawings (in which like numerals, if included, designate like parts). One can appreciate the many features that distinguish the instant invention from known devices and techniques. The drawings have been included to communicate the features of the innovative sensor apparatus structure and associated technique of the invention by way of example, only, and are in no way intended to unduly limit the disclosure hereof.

BRIEF DESCRIPTION OF ATTACHMENTS

Each of the following two identified enclosures, labeled ATTACHMENT A–B, is hereby fully incorporated herein by reference to the extent necessary to aid in a thorough understanding of the technical background and rigorous mathematical and engineering/test analysis performed by the applicants in support of their invention:

ATTACHMENT A is an indepth 13-page CONFIDENTIAL manuscript (January 2002) authored by the applicants entitled "*The Higher-Order Harmonics of a Magnetically-Soft Sensor: Application to Remote Query Temperature Measurement*", included herewith for its technical background and analysis and support of the invention.

ATTACHMENT B is a 5-page CONFIDENTIAL manuscript authored by the applicants entitled "*Theoretical Model Describing the Harmonic Response of Magnetically-Soft Ribbons*", included herewith for its technical background discussion and analysis in further support of the invention.

DETAILED DESCRIPTION OF THE PREFERRED EMBODIMENTS

Figure 1:
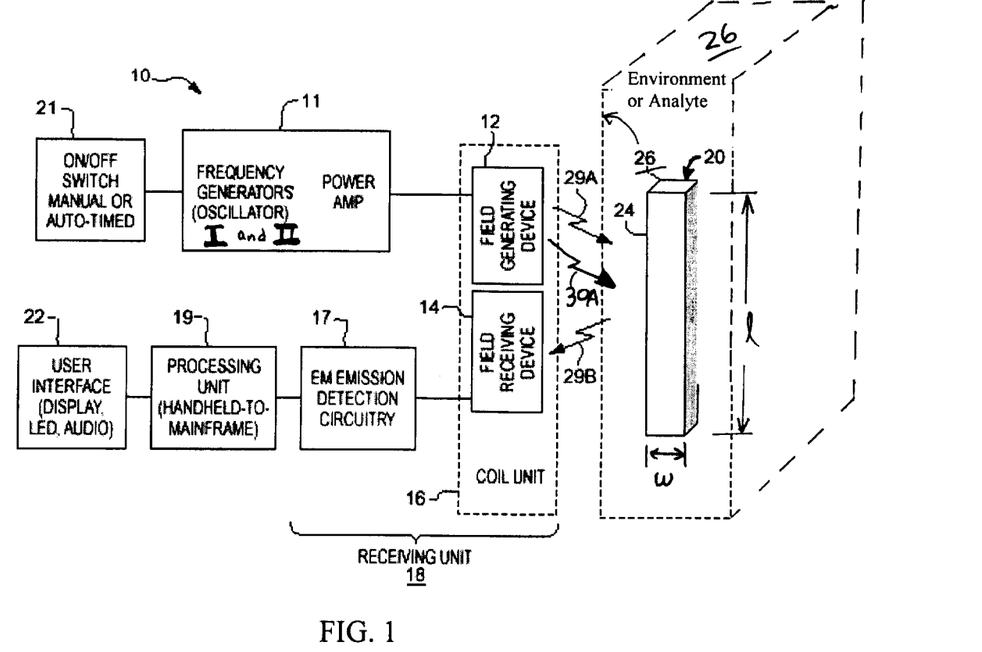
FIG. 1 schematically, in block diagram form, depicts components of an apparatus 10 of the invention for remote query utilizing amplitude values identified for the higher-order harmonic frequencies of interest emitted from a magnetically soft sensing element 20.

FIG. 1 schematically, in block diagram form, depicts components of an apparatus 10 of the invention for remote query utilizing amplitude values identified for the higher-order harmonic frequencies of interest emitted from a magnetically soft sensing element 20. Sensor structures similar to that depicted, enlarged for purposes of illustration at 20 (here, by way of example only, shaped as an elongated bar of width, w, and length, e), are located within or on a surface of the dashed-boundary 26 representing an environment or an analyte (i.e., substance undergoing analysis). Boundary 26 represents a multitude of different environments and analytes of varying sizes and conditions within which parameter of interest (temperature, stress conditions, or corrosion) will be measured. By way of example, the sensor may be located within an environment such as that encountered in a biomedical application or in monitoring of contaminants found in aqueous solution anlytes (such as groundwater, treated water, or wastewater whether flowing in natural or manmade waterways, canals, wells, or pipes), monitoring or measuring stress conditions or corrosion within construction materials (solid analytes), and so on.

In many applications, only one such sensor structure 20 is needed within an environment/analyte being sensed. As one can appreciate, a considerable range of sizes is available-preferably magnetically soft elements having a length, e, 1 mm to 1000 mm are contemplated. Where a "package" of sensing information is desired, several separate sensor structures can be located within the analyte (see FIG. 7), or an ordered array of sensor structures may be fabricated in an array (see FIG. 9 at 90) whether embedded within, interposed between laminate-layers, or atop a surface of a solid. Each sensor structure of such an array may be designed and built (sized/shaped and materials) to operate over a slightly different frequency range than the other sensors within the array; thus, making it easier to distinguish emissions received (or, "heard") from each particular sensor of the array.

The preferred sensing apparatus of the invention depicted in block form at 10 in FIG. 1 includes a transmitting subassembly 11 having at least two frequency generators or oscillators whose output is fed to a power amplifier which, in turn, feeds at least one time-varying field generating coil 12 capable of generating both time-varying interrogation fields 29A, 30A. One frequency generator (I) is used for generating the higher frequency time-varying interrogation field 29A and one (II) is used for generating the lower, quasi-static, time-varying field 30A. Preferably, the higher frequency generator (I) is capable of generating signals at frequencies ranging from 50 Hz to 10 MHz and the lower frequency (quasi-static, or effectively dc field) generator (II) is capable of generating signals at frequencies ranging from 0.1 Hz to 10 Hz. A receiving unit is depicted at 18 to include the receiving device 14 and EM emission detection circuitry 17. The field generating device 12 establishes alternating magnetic fields of desired frequency and amplitude in the area bounded by dashed line 26. The amplitude of the fields necessary to generate a predetermined signal level (sensor amplitude response) will vary depending upon system parameters such as coil size, sensor material, and sensitivity of receiving electronics. In operation, both the higher frequency field 29A and low frequency bias field 30A, consisting of dc and ac magnetic field components, around a sensor in operation to maximize the harmonic emission response thereof. One single coil unit 16 may be used to generate both interrogation fields as well as receive EM emissions 29B from sensor structure 20.

A receiving unit 18 is employed for measuring EM emissions emanating from the sensor. Suitable emission detection circuitry (represented by box 17) is in communication with a suitable EM field/emission receiving coil. EM pick-up coils suitable for use to operate up to 1 MHz are readily available. Information gathered about the environment/analyte by the receiving unit 18 is sent to a processing unit 19 (such as a dedicated microprocessor 39 in FIG. 2 controlled by software components or subroutines to perform data processing and manipulation) which is, in turn, connected to a user interface 22 of suitable type such as a monitor screen such as 42 in FIG. 2 (whether or not touch-sensitive) displaying alphanumeric or waveform information, one or more light emitting diode (LED) indicators (such as a display of color-coded LEDs), automatic audio message or siren, and so on. Depending upon the nature and location of the environment/analyte 26 being sensed, the user interface may necessarily be located nearby, or several hundreds of miles from the environment and processing unit 19 to communicate via digital phone line, coaxial cable, or satellite link.

Figure 2:
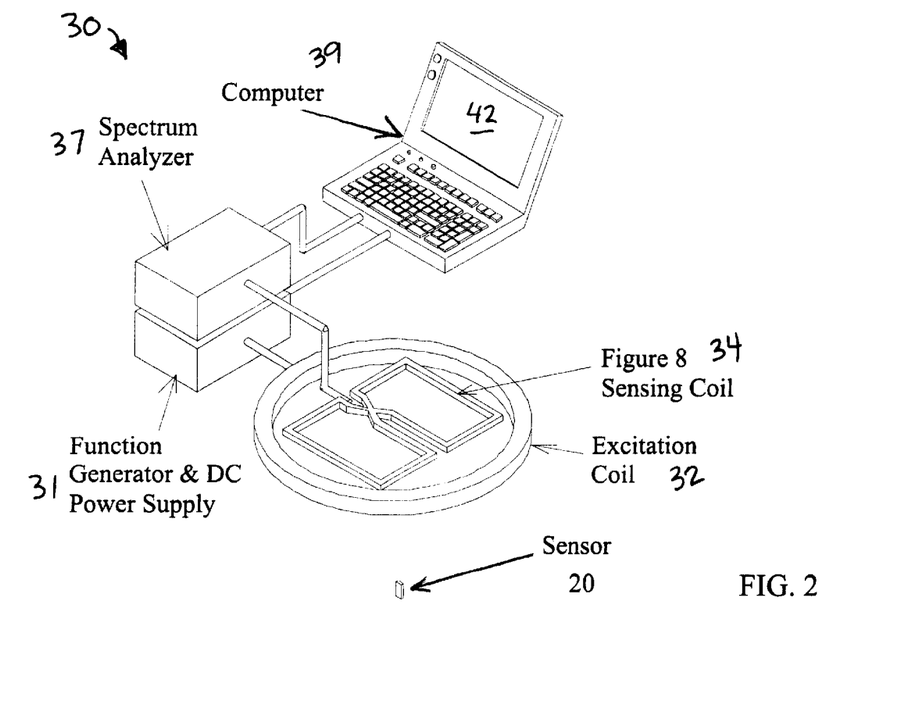
FIG. 2 schematically depicts representative components of an apparatus of the invention useful for monitoring EM emissions from sensor 20, with the harmonic amplitudes captured using a spectrum analyzer 37 to identify a parameter of interest within the environment/analyte 26 (FIG. 1) using a processor of computer 39.

FIG. 2 schematically depicts representative components of an apparatus of the invention 30 useful for monitoring EM emissions from sensor 20, with the harmonic amplitudes captured using a spectrum analyzer 37 to identify a parameter of interest within the environment/analyte 26 (FIG. 1) using a processor of computer 39. Function Generator and dc power supply (at 31) in conjunction with excitation coil 32 operate to generate suitable time-varying signals at requisite frequencies and amplitudes to excite sensor 20 to emit higher-order harmonic signals of detectable amplidutes.

Figure 3:
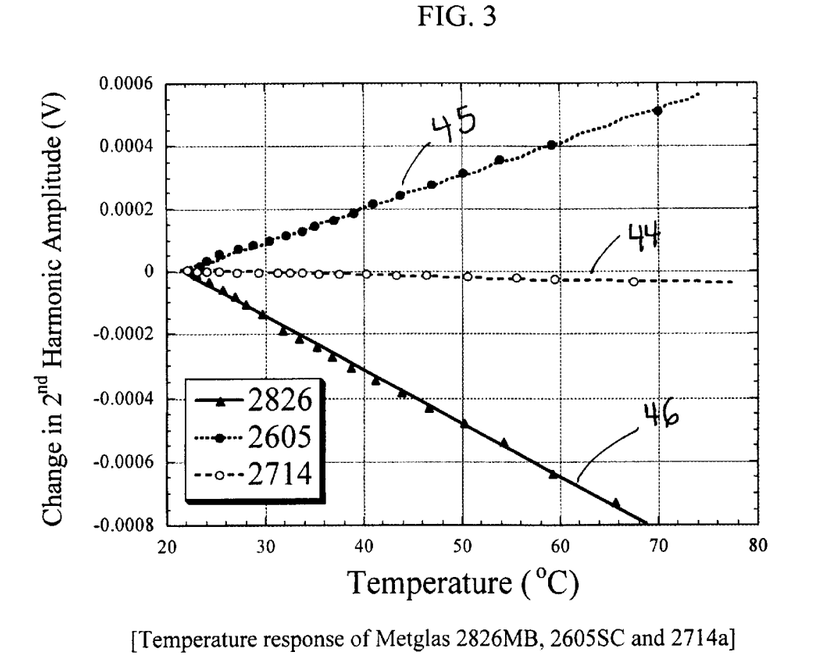
FIG. 3 graphically depicts correlations (change in $2^{nd}$ harmonic signal amplitude of sensor emissions as a function of temperature) made for elongated sensor elements of three different magnetically soft materials: comparative relative maximum harmonic amplitude values are plotted as a function of temperature.

FIG. 3 graphically depicts correlations (change in $2^{nd}$ harmonic signal amplitude of sensor emissions as a function of temperature) made for elongated sensor elements of three different magnetically soft materials. Here, comparative relative maximum harmonic amplitude values are plotted as a function of temperature. The curve 45 (representing the temperature response for the iron-rich material identified as METGLAS® 2605SC) and curve 46 (representing tempera-ture response for the iron-rich material METGLAS® 2826MB), show a large and linear change in signal amplitude as a function of temperature, while the cobalt-rich alloy METGLAS® 2714a remains relatively insensitive to temperature as it changes (curve 44). The sensor element exposed to a 200 Hz interrogation field and a quasi-static interrogation-biasing field; the latter being swept slowly (either sinusoidally or linearly up and down) while maximum amplitudes of the different higher-order harmonics are identified (preferably, sweeping to find a relative maximum amplitude for each order harmonic of interest) and compared. This can be performed by tracking relative changes in EM emission intensity between different, neighboring, higher-order harmonics.

Referring to ATTACHMENT A hereof as reported, the measured amplitudes of the $2^{nd}$ and $3^{rd}$ order harmonics from a sensor element of the invention, plotted as a function of applied dc field at 21° C. (room temperature) and at 75° C. illustrate that the signal amplitudes increase as temperature increases. Further plots of the peak amplitudes of the $2^{nd}$, $3^{rd}$, and $4^{th}$ order harmonics as a function of temperature indicate that the temperature response is linear, and the amplitude-temperature slopes vary with harmonic number.

Figure 4:
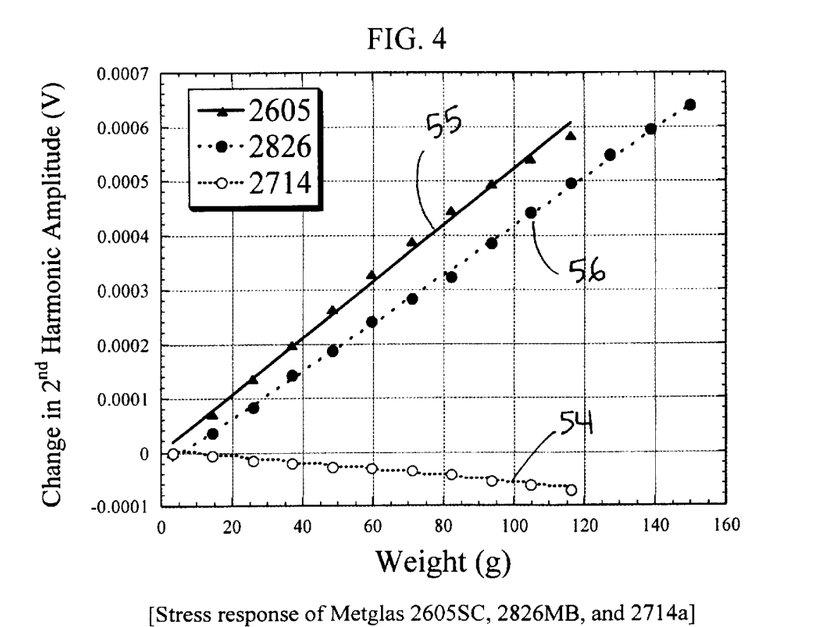
FIG. 4 graphically depicts correlations (change in $2^{nd}$ harmonic signal amplitude of sensor emissions as a function of weight applied by hanging larger and larger masses from an end of the sensor) made for elongated sensor elements of three different magnetically soft materials: comparative relative maximum harmonic amplitude values are plotted as a function of weight applied.

The temperature response of each higher-order harmonic in FIG. 4 of ATTACHMENT A was curve-fit to a function of temperature T with a linear equation. Here, the $2^{nd}$ and $3^{rd}$ order harmonics, $f_2$ and $f_3$, are used since they have higher measured signal amplitudes:

$$f_2 = \alpha(Ts_2 + a_2) \quad (1)$$

$$f_3 = \alpha(Ts_3 + a_3) \quad (2)$$

$\alpha$ is the zero crossing at the y-axis, s is the slope, and $\alpha$ is the scaling factor accounting for sensor location. Notice the same $\alpha$ is used in Eq. (1) and (2) since the location of the sensor has the same effect on all harmonics. The ratio of Eq. (1) to (2) yields:

$$T = \frac{f_3 a_2 - f_2 a_3}{f_2 s_3 - f_3 s_2} \quad (3)$$

A temperature calibration measurement is needed to obtain the coefficients $S_2$, $S_3$, $a_2$, and $a_3$; they are independent of sensor location.

For a given measurement the amplitudes of the $2^{nd}$ and $3^{rd}$ order harmonics, $f_2$ and $f_3$, are measured, with temperature determined by substituting $f_2$ and $f_3$ and the pre-determined coefficients into Eq. (3). Table 1 of ATTACHMENT A provides a listing of suitable temperature sensor coefficients. Taking the average of additional higher-order harmonic terms can further enhance the accuracy of the temperature measurement so that temperature, T, can be obtained from the expression:

$$T = \frac{1}{(N-1)^2 - N} \sum_{i=2}^{N} \sum_{j=2}^{N} \frac{f_i a_j - f_j a_i}{f_j s_i - f_i s_j} \quad i \neq j \quad (4)$$

where N is the highest harmonic used for averaging. N can range from 2 to a hundred if an extremely soft magnetic material and a sensitive interrogation system are used.

By way of example only, for purposes of experimental demonstration: three types of ribbons with different alloy composition, $Fe_{81}B_{13.5}Si_{3.5}C_2$ (METGLAS® 2605SC), $Fe_{40}Ni_{38}Mo_4B_{18}$ (METGLAS® 2826MB), and $Co_{65}Fe_4Ni_2Si_{15}B_{14}$ (METGLAS® 2714a), were tested. The experimental setup and results of stress, temperature, and chemical/corrosion monitoring follow. Referring, also, to FIG. 2, a sensor 20 of 5.5 cm×3.65 cm×30 mm was excited at 200 Hz by an excitation coil (36-turn, 14 gauge wire, 30 cm radius) connected to a Wavetek® 20 function generator to generate the ac signal, in series with a Kepco® dc power supply used to provide the dc biasing field. A figure-8 pickup coil (400-turn, 40 gauge wire, 15 cm×15 cm total area) co-planar with the interrogation coil was used to monitor the response of the sensor, with the harmonic amplitudes captured using a HP4293B spectrum analyzer 37. A computer 39 was used to automate the experiment.

To generate results of FIG. 3, the sensor element was inserted in a water-filled beaker atop a hot plate; amplitudes of the higher-order harmonics were measured while the temperature of the water was varied. The 2605SC (curve 45) has a positive temperature response (positive temperature slope) and 2826MB (curve 46) has a negative response: cause of this is a change in magnetic susceptibility with temperature (for ferromagnetic materials susceptibility and permeability are virtually equal). The magnetization of the sensor, which is proportional to the measured signal amplitude, can be expressed as:

$$m(t) = \frac{h_0^2}{2}\left[\chi_2 + \frac{3}{4}\chi_4 h_0^2\right] + h_0\left[\chi_1 + \frac{1}{4}\chi_3 h_0^2 + \frac{5}{8}\chi_5 h_0^4\right]\cos(\omega t) + \\ \frac{h_0^2}{2}[\chi_2 + \chi_4 h_0^2]\cos(2\omega t) + \frac{h_0^3}{4}\left[\chi_3 + \frac{5}{4}\chi_5 h_0^2\right]\cos(3\omega t) + \\ \frac{h_0^4}{8}\chi_4\cos(4\omega t) + \frac{h_0^5}{16}\chi_5\cos(5\omega t) + \ldots \quad (5)$$

Eq. (5) indicates the amplitude of the higher-order harmonic is proportional to the susceptibility $\chi$. For a high permeability, magnetically-soft ribbon, its susceptibility and permeability can be approximated as the slope of the bh-loop, equal to:

$$\chi \approx \mu = \frac{M_s}{H_k} \quad (6)$$

As temperature increases, the saturation magnetization $M_s$ of ferromagnetic materials decreases. However, the anisotropy field $H_k$ does not necessarily decreases with increasing temperature over the region investigated. Experimentally, $H_k$ of 2605SC was found to decrease with increasing temperature within the range of 21° C. to 75° C. As a result, the permeability of 2605SC increases with temperature. In contrast, $H_k$ of 2826MB was found to increase with temperature, resulting in a smaller permeability at high temperature with a decreasing harmonic amplitude. The permeability of 2714a remains stable with temperature between 21° C. and 75° C., hence it shows an almost zero response to temperature. The results shown in FIG. 3 include amplitude of the $2^{nd}$ order harmonic as a function of temperature. A more-exacting temperature value can be calculated using the expression described in ATTACHMENT A (Eq. 1 above), where a ratio of two or more higher-order harmonics is used to mitigate the effect of sensor location and orientation.

FIG. 4 graphically depicts correlations (change in $2^{nd}$ harmonic signal amplitude of sensor emissions as a function of weight applied by hanging larger and larger masses from an end of the sensor) made for elongated sensor elements of three different magnetically soft materials. Here, comparative relative maximum harmonic amplitude values are plotted as a function of weight applied. The curve 55 (representing the stress response for METGLAS® 2605SC) and curve 56 (representing stress response for METGLAS® 2826MB), show measurable linear positive stress response, while the cobalt-rich alloy METGLAS® 2714a has a negative smaller stress response (curve 54).

Figure 5:
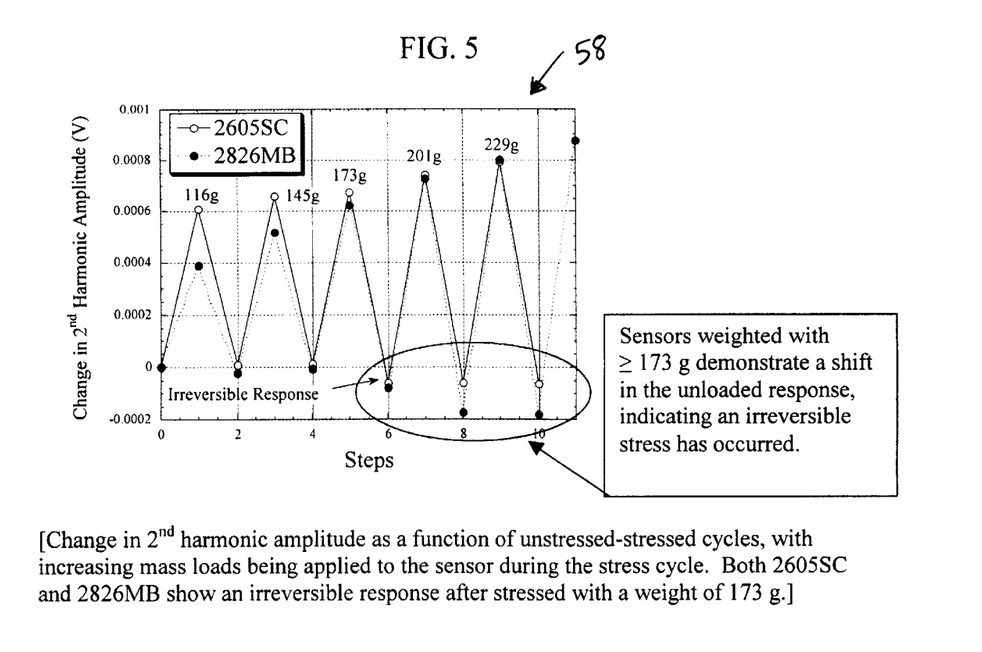
FIG. 5 graphically depicts correlations (labeled 58) representing the change in $2^{nd}$ harmonic amplitude identified as a function of unstressed-stressed cycles: comparative relative maximum harmonic amplitude values are plotted as a function of stress cycle steps.

FIG. 5 graphically depicts correlations (labeled 58) representing the change in $2^{nd}$ harmonic amplitude identified as a function of unstressed-stressed cycles. Here, comparative relative maximum harmonic amplitude values are plotted as a function of stress cycle steps. For purposes of experimental demonstration, a 'stress cycle' comprised increasing the mass load applied (hung from) then removed from the sensor element. One can see that once a 173g mass was applied to the sensor element, an irreversible stress (plastic deformation of the magnetically soft material) occurred thus affecting stress cycles monitored thereafter. The sensor used to detect stress conditions inside, for example, concrete structures that support buildings, highways, and bridges. Based on the irreversible response seen in FIG. 5, the harmonic sensor can be used to indicate if a concrete structure has been exposed to too large stress that has resulted in internal structural damage. Buildings that have been exposed to considerable stress, such as that associated with an earthquake or explosion, may be stressed close to their failure point while inspection of the concrete does not indicate is potential for failure. Placement of these stress sensors within the concrete enable remote query of stress conditions inside the concrete.

Figure 6:
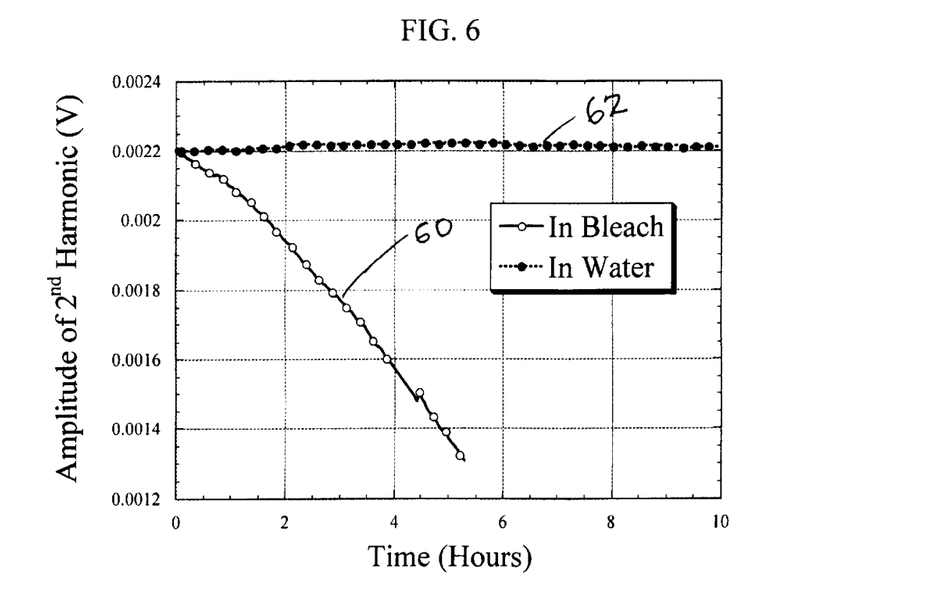
FIG. 6 graphically depicts correlations ($2^{nd}$ harmonic signal amplitudes of sensor emissions taken over time) made for elongated sensor elements of for METGLAS® 2605SC magnetically soft material.

FIG. 6 graphically depicts correlations ($2^{nd}$ harmonic signal amplitude of sensor emissions taken over time) made for elongated sensor elements of for METGLAS® 2605SC magnetically soft material: relative maximum harmonic amplitude values are plotted as a function of time. For purposes of experimental demonstration, data was collected for a sensor element immersed in a 6% hyperchlorite solution (60) and in water (62). As the chlorine in the solution corrodes the sensor element, its magnetization and permeability are reduced resulting in a change (decrease) in the $2^{nd}$ order harmonic amplitude of the sensor element in solution, exposed to a 200 Hz interrogation field and a quasi-static interrogation-biasing field. High or prolonged exposure to chlorine is damaging to concrete and other solid analytes. Hence the sensor can be used to monitor the corrosion level inside concrete structures, such as for example the supporting columns of bridges.

Figure 7:
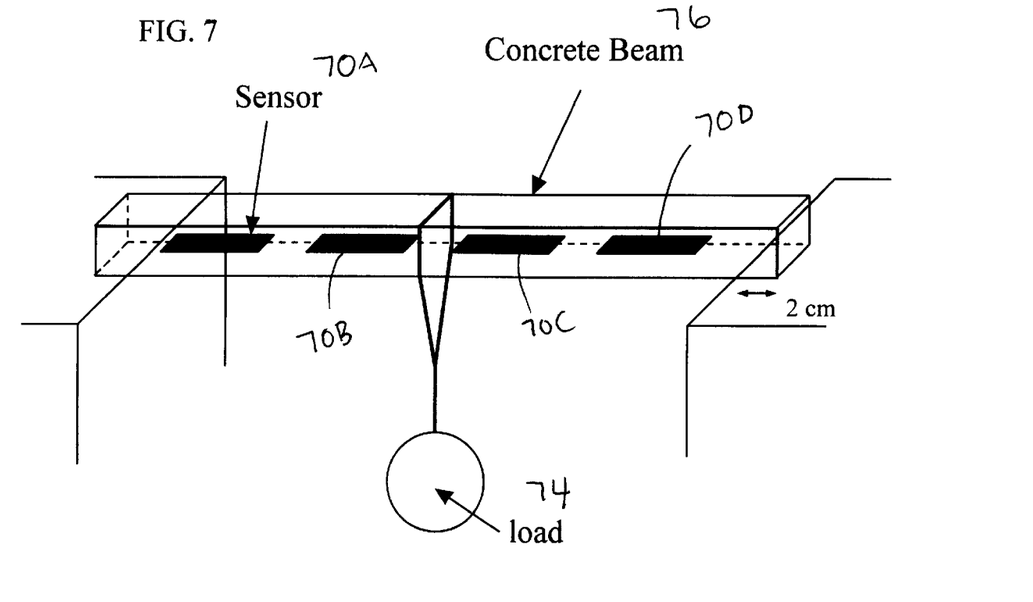
FIG. 7 is a schematic depicting METGLAS® 2605SC ribbon-shaped sensor elements (70A–70D) located within a solid analyte 76.

FIG. 7 is a schematic depicting METGLAS® 2605SC ribbon-shaped sensor elements (70A–70D) located within a solid analyte 76. Here, for purposes of experimental demonstration, data was collected for a concrete beam 76 within which several sensor elements 70A–70D are embedded. A load represented at 74 is applied at the central area of the beam-data is collected for varying weights 74 (representing the application of different stress levels to the solid beam). By way of example, only to generate results reported in FIG. 8, a concrete beam of 30 cm×5 cm×5 cm was fabricated from Quikrete® mortal mix. Sensors of 5.5 cm×3.65 mm×30 mm were embedded along the longitudinal axis of the concrete beam, and the beam was supported by its two ends as shown in FIG. 7.

Figure 8:
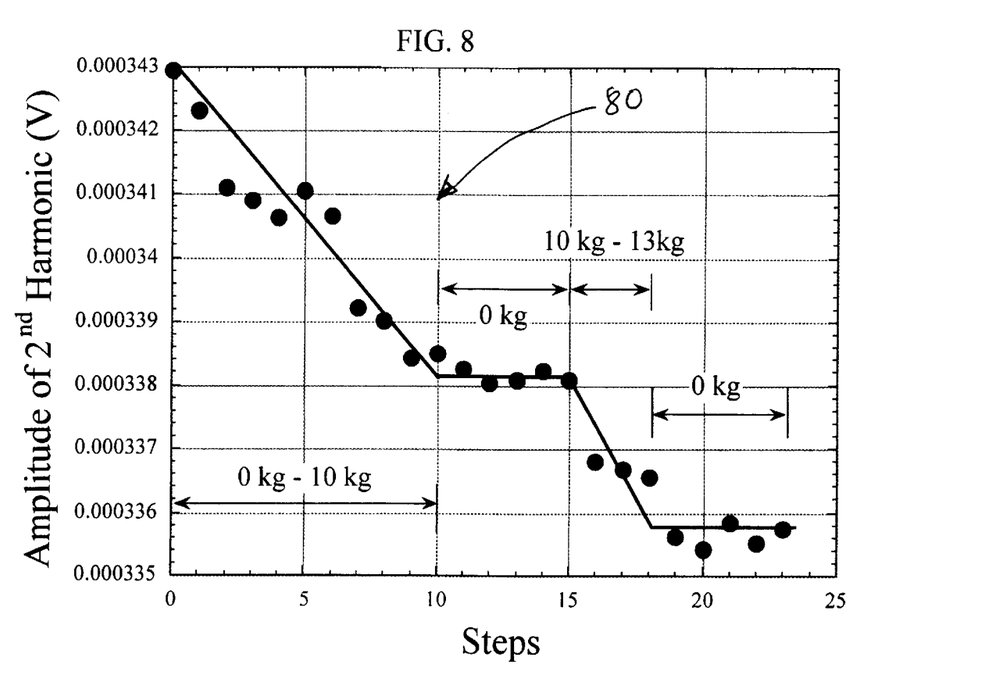
FIG. 8 graphically depicts a correlation (labeled 80) generated for purposes of experimental demonstration using the setup illustrated in FIG. 7, representing the $2^{nd}$ harmonic amplitude identified as a function of stress loading/'steps'.

FIG. 8 graphically depicts a correlation (labeled 80) generated for purposes of experimental demonstration using the setup illustrated in FIG. 7, representing the relative maximums of the $2^{nd}$ harmonic amplitude identified plotted as a function of stress loading, labeled 'steps'. As depicted here at 80, a decrease in harmonic signal amplitude occurs with increasing stress. Compare 80 to the correlation at 55 FIG. 4 (harmonic signal amplitude increases with increasing load applied) where the stress is directly applied to the test sensor element (vertically oriented as shown in FIG. 9 at 94) by hanging the load from a lower-end of the vertically oriented hanging element.

A four-stage experiment was conducted and maximum amplitude of the $2^{nd}$ harmonic was tracked as a function of increasing stress on the sensor (see FIG. 8): {1} During the first stage, the weight of the load was increased in 1 kg increments until the total weight reached 10 kg; the response of the sensor was monitored after each increment. As seen in FIG. 8, the increasing weight linearly stresses the embedded sensors within the bar. {2} The 10 kg load was then removed from the beam and the response of the sensor was measured five different times. The response of the sensors stays fixed at the maximum stress level, indicating an irreversible stress within the concrete. {3} The load weight was then increased from 10 kg to 13 kg, with the sensor response measured after each 1 kg increment. {4} After reaching 13 kg the weight was removed and the sensors measured; the flat response of the sensor indicates the stress level within the concrete is irreversible. Employing the harmonic sensor technique of the invention, one can see a change in the signal amplitude when the concrete beam was exposed to a stress, even where there is no observable damage or indication of deformation from visually inspecting the outside surface. Hence, the harmonic sensor provides an effective way to detect internal damages of concrete structures such as buildings, bridges, roadways, etc.

Figure 9:
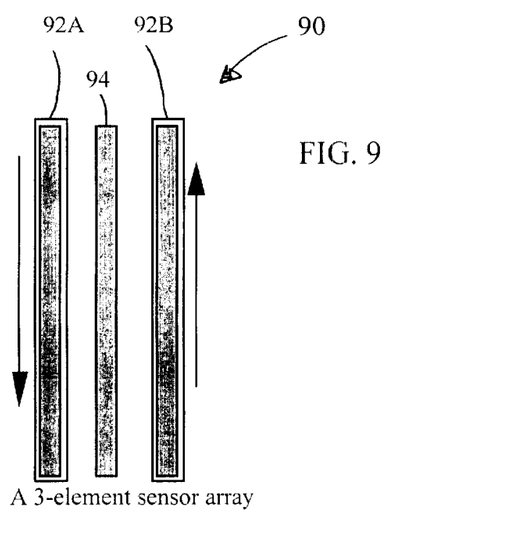
FIG. 9 schematically represents a sensor element 94 interposed between two MH elements 92A, 92B as array 90.
Figure 10:
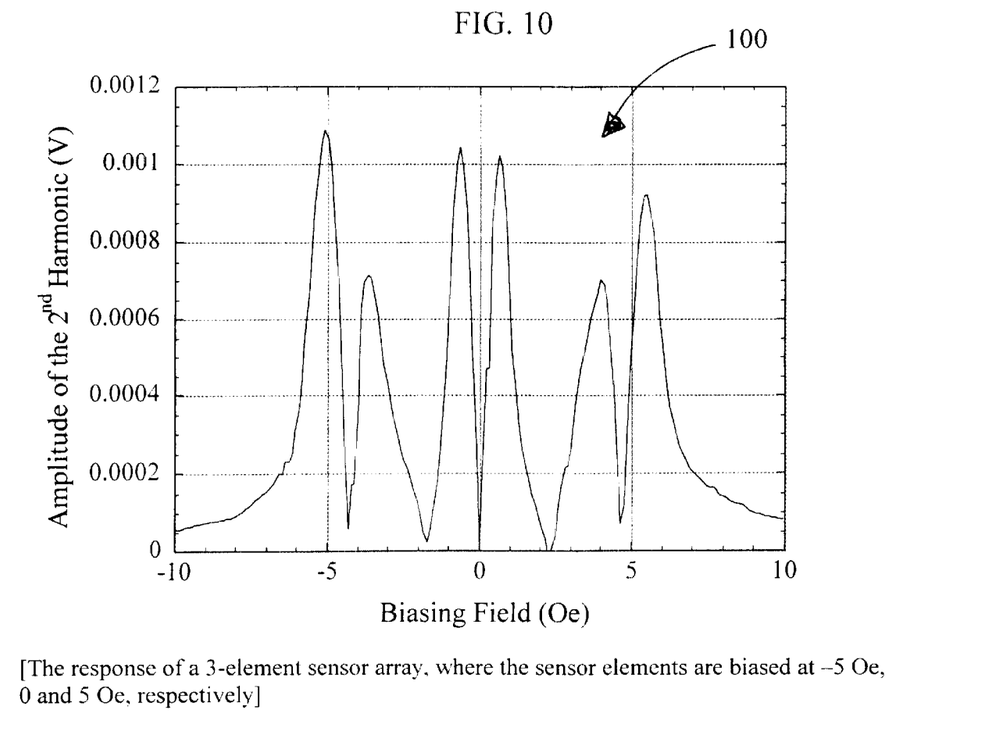
FIG. 10 graphically depicts the harmonic response for array 90 of FIG. 9; amplitude of the $2^{nd}$-order harmonic measured by detecting electromagnetic emissions from the sensor array, is plotted against biasing field—element signatures identifiable.

FIG. 9 schematically represents a sensor element 94 interposed between two MH elements 92A, 92B as array 90. The elements are biased as follows: element 92A biased at −5 Oe, magnetically soft element 94 is unbiased, and element 92B at +5 Oe. Ferrites generally have stray magnetic fields of several tens of Oersteds (Oe); their stochiometric composition can be varied to enable the stray field they support to change with chemical exposure. Hence when a 'designer' MH biasing elements are used in combination with a magnetically-soft sensing element, the biasing field turn-on point determined by the MH biasing element can be used as an indicator of background chemistry concentration. FIG. 10 graphically depicts the harmonic response for the array of FIG. 9; amplitude of the $2^{nd}$-order harmonic measured by detecting electromagnetic emissions from the sensor array 90, is plotted against biasing field. Relative maximum amplitudes can be spotted, as plotted-making signatures of each separate element of the array 90 are readily identifiable.

Magnetic material/substances exhibit magnetic and elastic phenomena. Magnetic interaction depend of the distance of the interacting particles and consequently magnetic and mechanic effected interact. In ferromagnetic materials, magnetostriction is observed: The dimensions and elastic properties of magnetic materials often depend on the state of magnetization (direct magnetoelastic effect). Materials that possess both effects, especially magnetically soft ferromagnetic materials (i.e. materials having a low coercive forces), are commonly referred to as magnetoelastic materials.

Generation of the higher order harmonics is purely an electromagnetic response based upon the permeability of the magnetically soft material, and not dependent upon the sensor mechanically vibrating; consequently the sensor can be encased within plastics, cement, glue, etc. without affecting the generation of higher-order harmonics. For the most part, overall sensor element length does not affect the harmonic response except as to total harmonic signal amplitude (a physically larger sensor element to provide greater signal than a physically smaller sensor element), or if the size of the sensor is reduced to a point that the demagnetizing field (associated with all magnetic materials) reduces the permeability of the material. Magnetically soft alloys are those that become magnetized readily upon application of a field and that return to effectively a nonmagnetic condition when the applied field is removed. The magnetically soft alloys currently widely available for use and testing are ferromagnetic, or ferrous, alloys characterized by their properties of high magnetic permeability, low coercive force and low magnetic hysteresis loss. Magnetically hard (MH) alloys, generally ferromagnetic, are those capable of being magnetized permanently because of an ability to retain induced magnetization and magnetic poles after removal of externally applied fields-MH alloys have high coercive force. The space around a MH material has a 'stray' bias/biasing field. The word "hard" was adopted based on the fact that the quality of early permanent magnets was related to their hardness. Suitable magnetically hard materials include ferromagnetic metal alloys and their oxides, capable of supporting sufficient external stray fields.

The material for the MH biasing element may be chosen for its selective response to a background chemical species or a corrosive undergoing analysis. This selective response will cause a change in the material characteristics of the MH element in turn changing the DC bias field supported by the MH biasing element, which due to its proximity to the magnetically soft sensing element, changes the EM emissions radiated therefrom. Alternatively, the material for the MH biasing element may be chosen for its stray field to offset background radiation noise in the event the sensing element is located in a particularly 'noisy' environment or solid analye. Whether a MH element is employed for its supporting bias field, according to the invention, it is the harmonic frequency response of the EM emissions remotely measured or detected for which an amplitude is identified to provide the sensing or monitoring information.

There are many magnetically soft materials currently available that may be used to construct a sensing element of the invention. Suitable amorphous metallic (glassy) alloys are commercially available under the brand names of MET-GLAS® (a registered trademark of Honeywell International, Inc.) and SENSORVAC® (a registered trademark of Vacuumschmelze (VAC) Corporation) alloys. One amorphous cobalt-based alloy known commercially as METGLAS® 2826MB (distributed by Allied Signal, Inc. in New Jersey) is vacuum annealed in the presence of a DC magnetic field to enhance magnetostriction. Another available magnetostrictive amorphous cobalt-based magnetically soft alloy is known commercially as ATALANTE® film, distributed by Innovative Sputtering Technology N.V. of Karreweg, Belgium (this film is used throughout Europe in anti-theft retail item markers). In the case of the sensor element used for collecting information about stress conditions and corrosion, it is preferable to choose a magnetically soft material, such as a cobalt-based one, that remains relatively stable (i.e., the material is generally insensitive to temperature fluxes) over the expected range of operating temperatures. It is preferable to choose an iron-rich magnetically soft material for the sensor element used as a temperature sensor.

By way of further background: The central processing unit (CPU) is the computing part of the computer. Also often referred to simply as the processor, a CPU it is made up of the control unit and an arithmetic logic unit (ALU)—a high-speed circuit that does calculating and comparing. Numbers are transferred from memory into the ALU for calculation, and the results are sent back into memory. Alphanumeric data is sent from memory into the ALU for comparing. The CPUs of almost all computers are contained on a single chip. As is well known, the basic elements of a simple computer include a CPU, clock and main memory; whereas a complete computer system requires the addition of control units, input, output and storage devices, as well as an operating system. Computer professionals involved with mainframes and microcomputers sometimes refer to the whole computer as the CPU, in which case, CPU refers to the processor, memory. (RAM) and I/O architecture (channels or buses). Once the data is in a computer's memory, the computer can process it by calculating, comparing and copying it; generally understood as follows: calculating—performing any mathematical operation on data by adding, subtracting, multiplying and dividing one set with another; comparing—analysis and evaluation of data by matching it with sets of known data that are included in a program or called in from storage; and coping—the moving of data around to create any kind of report or listing, etc., in a selected order.

While certain representative embodiments and details have been shown merely for the purpose of illustrating the invention, those skilled in the art will readily appreciate that various modifications, whether specifically identified herein, may be made to these representative embodiments without departing from the novel teachings or scope of this technical disclosure. Accordingly, all such modifications are intended to be included within the scope of the claims. Although the commonly employed preamble phrase "comprising the steps of" may be used herein, or hereafter, in a method claim, the Applicants do not intend to invoke 35 U.S.C. Section 112 §6. Furthermore, in any claim that is filed herewith or hereafter, any means-plus-function clauses used, or later found to be present, are intended to cover at least all structure(s) described herein as performing the recited function and not only structural equivalents but also equivalent structures.

What is claimed is:

1. A temperature sensing apparatus, comprising:
   a sensor element made of a magnetically soft material operatively arranged within a first and second time-varying interrogation magnetic field, said first time-varying magnetic field being generated at a frequency higher than that for said second magnetic field;
   a receiver, remote from said sensor element, to measure intensity of electromagnetic emissions from said sensor element to identify a relative maximum amplitude value for each of a plurality of higher-order harmonic frequency amplitudes so measured; and
   a unit to determine a value for temperature using said relative maximum harmonic amplitude values identified.

2. The apparatus of claim 1 wherein said higher frequency of said first field is at least ten times greater than said second magnetic field frequency; said unit comprises a processor, and said temperature value, T, is determined according to the expression:

$$T = \frac{1}{(N-1)^2 - N} \sum_{i=2}^{N} \sum_{j=2}^{N} \frac{f_i a_j - f_j a_i}{f_j s_i - f_i s_j} \quad i \neq j.$$

3. The apparatus of claim 1 wherein said receiver comprises an electromagnetic pick-up coil and a spectrum analyzer, said sensor element is elongated in shape, and a pre-correlation made between a series of comparative relative maximum harmonic amplitude values and a corresponding series of temperature values is used to determine said temperature value.

4. The apparatus of claim 3 wherein a width, w, of said elongated sensor element is less than three times a length thereof, e; said receiver further comprises a spectrum analyzer, and said pre-correlation was made for a calibration sensor element of like size and material characteristics of said sensor element.

5. The apparatus of claim 1 wherein said higher frequency of said first field is selected from a first range of frequencies from 50 Hz to 10 MHz and said frequency of said second field is selected from a second range of frequencies from 0.1 Hz to 10 Hz; and further comprising a computerized device for instructing said receiver to take, over a time interval, a series of sensor element emission measurements, and communicate each of a series of corresponding temperature values for said series of emission measurements taken.

6. The apparatus of claim 1 wherein the sensor element is located within a solid analyte, said value for temperature represents a localized temperature of said solid analyte, and said solid analyte comprises a component of a material selected from the group consisting of concrete, mortar, tar, wood, fiberboard, particleboard, plasterboard, sheetrock, fiberglass, plexiglass, resins, and plastics.

7. The apparatus of claim 6 wherein:
   the said sensor element is elongated, having a length, e, from 1 mm to 1000 mm, and is made of a ferromagnetic alloy;
   said solid analyte comprises a laminate of at least two components from said group; and
   said sensor element is at least partially encapsulated within a corrosion-resistant casing and is interposed between said two components.

8. The apparatus of claim 6 wherein the said sensor element is elongated, having a length, e, from 1 mm to 1000 mm, and is embedded within said solid analyte, and said temperature value, T, is determined according to the expression:

$$T = \frac{1}{(N-1)^2 - N} \sum_{i=2}^{N} \sum_{j=2}^{N} \frac{f_i a_j - f_j a_i}{f_j s_i - f_i s_j} \quad i \neq j.$$

9. The apparatus of claim 1 wherein the sensor element is located on a surface of a solid analyte, said value for temperature represents a localized surface temperature of said solid analyte, and said solid analyte comprises a component of a material selected from the group consisting of concrete, mortar, tar, wood, fiberboard, particleboard, plasterboard, sheetrock, fiberglass, plexiglass, resins, and plastics.

10. The apparatus of claim 1 further comprising a magnetically hard element supporting a biasing field adjacent said magnetically soft sensor element, said magnetically hard element comprised of a material chemically responsive to a fluid analyte such that exposure thereto causes a change in said biasing field.

11. The apparatus of claim 1 wherein said first time-varying interrogation magnetic field comprises a signal-burst generated at said higher frequency, said measure of emissions is performed while sweeping said second time-varying field and while said signal-burst is transmitted by an interrogation field generating coil, said interrogation field generating coil is adapted for generating said second field, and said plurality of higher-order harmonic amplitudes so measured are for harmonics selected from a range of 2 to 100 times a fundamental resonant frequency for said sensor element.

12. An apparatus for sensing stress conditions of a solid analyte, comprising:
- a sensor element made of a magnetically soft material operatively arranged within a first and second time-varying interrogation magnetic field, said first time-varying magnetic field being generated at a frequency higher than that for said second magnetic field;
- a receiver, remote from said sensor element, to measure intensity of electromagnetic emissions from said sensor element to identify a relative maximum amplitude value for each of a plurality of higher-order harmonic frequency amplitudes so measured; and
- a unit to determine a value for stress conditions of the analyte in proximity to said sensor element using said relative maximum harmonic amplitude values identified.

13. The apparatus of claim 12 wherein said higher frequency of said first field is at least ten times greater than said second magnetic field frequency; said unit comprises a processor, said magnetically soft material comprises a ferromagnetic alloy, and a pre-correlation made for a calibration sensor element of like size and material characteristics of said sensor element is used to determine said stress conditions value.

14. The apparatus of claim 12 wherein said higher frequency of said first field is selected from a first range of frequencies from 50 Hz to 10 MHz and said frequency of said second field is selected from a second range of frequencies from 0.1 Hz to 10 Hz; and further comprising a computerized device for instructing said receiver to take, over a time interval, a series of sensor element emission measurements, and communicate each of a series of corresponding stress condition values for said series of emission measurements taken.

15. The apparatus of claim 12 wherein the sensor element is made of a ferromagnetic alloy, is elongated, and is located within a solid analyte, and said value for stress conditions represents a localized stress within said solid analyte.

16. The apparatus of claim 15 wherein:
- said sensor element is embedded within said solid analyte, said solid analyte comprises a component of a material selected from the group consisting of concrete, mortar, tar, wood, fiberboard, particleboard, plasterboard, sheetrock, fiberglass, plexiglass, resins, and plastics;
- said plurality of higher-order harmonic amplitudes so measured are for harmonics selected from a range of 2 to 100 times a fundamental resonant frequency for said sensor element; and
- said sensor element is at least partially encapsulated within a corrosion-resistant casing.

17. The apparatus of claim 12 wherein the sensor element is located on a surface of a solid analyte, said value for stress conditions represents a localized surface stress of said solid analyte, and said solid analyte comprises a component of a material selected from the group consisting of concrete, mortar, tar, wood, fiberboard, particleboard, plasterboard, sheetrock, fiberglass, plexiglass, resins, and plastics.

18. The apparatus of claim 12 further comprising a magnetically hard element supporting a biasing field adjacent said magnetically soft sensor element, said magnetically hard element comprised of a material chemically responsive to a fluid analyte such that exposure thereto causes a change in said biasing field.

19. The apparatus of claim 12 wherein said first time-varying interrogation magnetic field comprises a signal-burst generated at said higher frequency, said measure of emissions is performed while sweeping said second time-varying field and while said signal-burst is transmitted by an interrogation field generating coil, said interrogation field generating coil is adapted for generating said second field, and said plurality of higher-order harmonic amplitudes so measured are for harmonics selected from a range of 2 to 100 times a fundamental resonant frequency for said sensor element.

20. An apparatus for monitoring a corrosive, comprising:
- a sensor element made of a magnetically soft material operatively arranged within a first and second time-varying interrogation magnetic field, said first time-varying magnetic field being generated at a frequency higher than that for said second magnetic field;
- a receiver, remote from said sensor element, to measure intensity of electromagnetic emissions from said sensor element to identify a relative maximum amplitude value for each of a plurality of higher-order harmonic frequency amplitudes so measured; and
- a unit to determine a value for corrosion in proximity to said sensor element using said relative maximum harmonic amplitude values identified.

21. The apparatus of claim 20 wherein said higher frequency of said first field is at least ten times greater than said second magnetic field frequency; said unit comprises a processor, said magnetically soft material comprises a ferromagnetic alloy, and a pre-correlation made for a calibration sensor element of like size and material characteristics of said sensor element is used to determine said corrosion value.

22. The apparatus of claim 20 wherein said higher frequency of said first field is selected from a first range of frequencies from 50 Hz to 10 MHz and said frequency of said second field is selected from a second range of frequencies from 0.1 Hz to 10 Hz; and further comprising a computerized device for instructing said receiver to take, over a time interval, a series of sensor element emission measurements to produce a corrosion response profile comprising a series of corresponding corrosion values for said series of emission measurements taken.

23. The apparatus of claim 20 wherein: said sensor element is located within an analyte; a pre-correlation made between a series of comparative relative maximum harmonic amplitude values, represented by a plurality voltages corresponding to certain of said emission intensity measurements taken, and a corresponding series of values representing concentration of the corrosive is used to determine said corrosion value.

24. The apparatus of claim 20 wherein the sensor element is made of a ferromagnetic alloy, is elongated, and is located within a solid analyte, and said value for corrosion represents a localized concentration of the corrosive within said solid analyte.

25. The apparatus of claim 20 wherein: said sensor element is located within a solid analyte, said solid analyte comprises a component of a material selected from the group consisting of concrete, mortar, tar, wood, fiberboard, particleboard, plasterboard, sheetrock, fiberglass, plexiglass, resins, and plastics; said plurality of higher-order harmonic amplitudes so measured are for harmonics selected from a range of 2 to 100 times a fundamental resonant frequency for said sensor element; and said receiver comprises an electromagnetic pick-up coil.

26. The apparatus of claim 20 wherein said sensor element is at least partially encapsulated within a corrosion-resistant casing; and further comprising a magnetically hard element supporting a biasing field adjacent said magnetically soft sensor element, said magnetically hard element comprised of a material chemically responsive to a fluid analyte such that exposure thereto causes a change in said biasing field.

27. The apparatus of claim 20 wherein the sensor element is located on a surface of a solid analyte, said value for corrosion represents a localized surface degradation of said solid analyte, and said solid analyte comprises a component of a material selected from the group consisting of concrete, mortar, tar, wood, fiberboard, particleboard, plasterboard, sheetrock, fiberglass, plexiglass, resins, and plastics.

28. The apparatus of claim 19 wherein said first time-varying interrogation magnetic field comprises a signal-burst generated at said higher frequency, said measure of emissions is performed while sweeping said second time-varying field and while said signal-burst is transmitted by an interrogation field generating coil, and said plurality of higher-order harmonic amplitudes so measured are for harmonics selected from a range of 2 to 100 times a fundamental resonant frequency for said sensor element.

* * * * *